(12) United States Patent
Babaie et al.

(10) Patent No.: US 11,473,972 B2
(45) Date of Patent: Oct. 18, 2022

(54) MONITORING LIGHT OUTPUT FROM AT LEAST ONE SOLID-STATE LIGHT SOURCE

(71) Applicant: ACUVA TECHNOLOGIES INC., Burnaby (CA)

(72) Inventors: Ashkan Babaie, Vancouver (CA); Ali Shagerdmootaab, Burnaby (CA)

(73) Assignee: ACUVA, TECHNOLGIES INC., Vancouver (CA)

( * ) Notice: Subject to any disclaimer, the term of this patent is extended or adjusted under 35 U.S.C. 154(b) by 373 days.

(21) Appl. No.: 16/650,105

(22) PCT Filed: Sep. 25, 2018

(86) PCT No.: PCT/CA2018/051211
§ 371 (c)(1),
(2) Date: Mar. 24, 2020

(87) PCT Pub. No.: WO2019/056136
PCT Pub. Date: Mar. 28, 2019

(65) Prior Publication Data
US 2020/0225088 A1 Jul. 16, 2020

(30) Foreign Application Priority Data

Sep. 25, 2017 (CA) .................................. CA 2980361

(51) Int. Cl.
| | |
|---|---|
| *G01J 1/42* | (2006.01) |
| *A61L 2/10* | (2006.01) |
| *A61L 2/26* | (2006.01) |
| *A61L 9/20* | (2006.01) |
| *C02F 1/32* | (2006.01) |
| *G01J 1/04* | (2006.01) |

(52) U.S. Cl.
CPC ................. *G01J 1/429* (2013.01); *A61L 2/10* (2013.01); *A61L 2/26* (2013.01); *A61L 9/20* (2013.01); *C02F 1/325* (2013.01); *G01J 1/0414* (2013.01); *A61L 2202/14* (2013.01); *A61L 2209/111* (2013.01); *A61L 2209/12* (2013.01); *C02F 2201/3222* (2013.01); *C02F 2201/3228* (2013.01); *G01J 2001/4252* (2013.01)

(58) Field of Classification Search
CPC .. G01J 1/429; G01J 1/0414; G01J 2001/4252; A61L 2/10; A61L 2/26; A61L 9/20; A61L 1101/14; A61L 2209/111; A61L 2209/12; C02F 1/325; C02F 2201/3222; C02F 2201/3228
USPC ........................... 250/453.11, 454.11, 455.11
See application file for complete search history.

(56) References Cited

U.S. PATENT DOCUMENTS

| | | | |
|---|---|---|---|
| 6,707,542 B1 * | 3/2004 | Cotton .................... | G01N 21/43 356/136 |
| 2003/0052272 A1 * | 3/2003 | Kiuchi ............... | G01N 21/3577 250/339.12 |
| 2011/0240886 A1 * | 10/2011 | Tokhtuev .............. | G01J 1/0271 250/573 |

* cited by examiner

Primary Examiner — Nicole M Ippolito
(74) Attorney, Agent, or Firm — Kilpatrick Townsend & Stockton LLP

(57) ABSTRACT

A method of monitoring light output from at least one solid-state light source involves sensing any light produced by the at least one solid-state light source and reflected, by at least one surface spaced apart from the at least one solid-state light source, to at least one reference location spaced apart from the at least one surface. Apparatuses and uses of the apparatuses are also disclosed.

20 Claims, 6 Drawing Sheets

MONITORING LIGHT OUTPUT FROM AT LEAST ONE SOLID-STATE LIGHT SOURCE

CROSS-REFERENCE TO RELATED APPLICATION

This application claims the benefit of, and priority to, Canadian patent application no. 2,980,361 filed Sep. 25, 2017, the entire contents of which are incorporated by reference herein.

FIELD

This disclosure relates generally to monitoring light output from at least one solid-state light source.

RELATED ART

Fluids, such as water or air for example, may be treated, for example to deactivate pathogens, by subjecting the fluid to UV light, and solid-state light sources such as light-emitting diodes ("LEDs") may produce such UV light. However, LEDs can fail or become less effective, either of which may go unnoticed. As a result, fluid may unknowingly not be treated or may be inadequately treated, which can result, for example, in health hazards. For instance, pathogens may not be sufficiently deactivated, if LEDs fail or become less effective in a fluid treatment apparatus.

SUMMARY

In accordance with one illustrative embodiment of the invention, there is provided a method of monitoring light output from at least one solid-state light source. The method may include sensing any light produced by the at least one solid-state light source and reflected, by at least one surface spaced apart from the at least one solid-state light source, to at least one reference location spaced apart from the at least one surface.

The method may further include producing at least one sensor signal representing sensing light produced by the at least one solid-state light source and reflected by the at least one surface to the at least one reference location.

Sensing may include sensing no light produced by the at least one solid-state light source and reflected by the at least one surface to the at least one reference location.

The method may include producing at least one sensor signal representing sensing no light produced by the at least one solid-state light source and reflected by the at least one surface to the at least one reference location.

The method may further include producing at least one error signal in response to the sensor signal representing sensing no light produced by the at least one solid-state light source and reflected by the at least one surface to the at least one reference location.

The method may further include producing at least one error signal in response to the sensor signal representing sensing no light produced by the at least one solid-state light source and reflected by the at least one surface to the at least one reference location when an electric potential is applied across the at least one solid-state light source to cause the at least one solid-state light source to produce light.

Sensing may comprise sensing a level of light produced by the at least one solid-state light source and reflected by the at least one surface to the at least one reference location.

The method may further include producing at least one sensor signal representing the level of light.

The method may further include producing at least one error signal in response to the sensor signal representing sensing the level of light below a threshold level.

The method may further include producing at least one error signal in response to the sensor signal representing sensing the level of light below a threshold level when an electric potential is applied across the at least one solid-state light source to cause the at least one solid-state light source to produce light.

Sensing any light produced by the at least one solid-state light source and reflected by the at least one surface may include sensing any ultraviolet ("UV") light produced by the at least one solid-state light source and reflected by the at least one surface.

The at least one solid-state light source may be a single solid-state light source.

The at least one reference location may be a single reference location.

The at least one reference location may be outside of an entire space between the at least one solid-state light source and at least one translucent body positioned to transmit a portion of any light produced by the at least one solid-state light source.

The at least one surface may include at least one surface of the at least one translucent body, and sensing any light produced by the at least one solid-state light source and reflected by the at least one surface to the at least one reference location may include sensing any light produced by the at least one solid-state light source and reflected by the at least one surface of the at least one translucent body to the at least one reference location.

The at least one surface may include at least one surface of at least one translucent body positioned to transmit a portion of any light produced by the at least one solid-state light source, and sensing any light produced by the at least one solid-state light source and reflected by the at least one surface to the at least one reference location may include sensing any light produced by the at least one solid-state light source and reflected by the at least one surface of the at least one translucent body to the at least one reference location.

The at least one translucent body may include at least one lens.

The at least one translucent body may include at least one window.

The at least one surface may include at least one reflective surface of at least one reflective body, and sensing any light produced by the at least one solid-state light source and reflected by the at least one surface to the at least one reference location may include sensing any light produced by the at least one solid-state light source and reflected by the at least one reflective surface of the at least one reflective body to the at least one reference location.

The at least one surface may include at least one reflective surface of at least one opaque body, and sensing any light produced by the at least one solid-state light source and reflected by the at least one surface to the at least one reference location may include sensing any light produced by the at least one solid-state light source and reflected by the at least one reflective surface of the at least one opaque body to the at least one reference location.

The at least one surface may include at least one surface of an optical head including the at least one solid-state light source and the at least one reference location.

The light reflected by the at least one surface may include light reflected by the at least one surface by specular reflection.

The light reflected by the at least one surface may include light reflected by the at least one surface by diffuse reflection.

The at least one solid-state light source and the at least one reference location may be on a same device.

The at least one solid-state light source and the at least one reference location may be on a same printed circuit board ("PCB").

The at least one solid-state light source may include at least one light-emitting diode ("LED").

In accordance with a further illustrative embodiment of the invention, there is provided a method of treating a fluid. The method may include monitoring light output from the at least one solid-state light source when the fluid is in a reaction chamber and positioned to receive light from the at least one solid-state light source.

The at least one surface may include at least one surface of the reaction chamber.

In accordance with a further illustrative embodiment of the invention, there is provided an apparatus for producing light output and for monitoring light output from the apparatus. The apparatus may include: at least one solid-state light source; and a sensing means for sensing any light produced by the at least one solid-state light source and reflected, by at least one surface spaced apart from the at least one solid-state light source, to at least one reference location spaced apart from the at least one surface.

The apparatus may further include a means for producing at least one error signal in response to the sensing means sensing no light produced by the at least one solid-state light source and reflected by the at least one surface to the at least one reference location.

The apparatus may further include a means for producing at least one error signal in response to the sensing means sensing no light produced by the at least one solid-state light source and reflected by the at least one surface to the at least one reference location when an electric potential is applied across the at least one solid-state light source to cause the at least one solid-state light source to produce light.

The apparatus may further include a means for producing at least one error signal in response to the sensing means sensing the level of light below a threshold level.

The apparatus may further include a means for producing at least one error signal in response to the sensing means sensing the level of light below a threshold level when an electric potential is applied across the at least one solid-state light source to cause the at least one solid-state light source to produce light.

The at least one solid-state light source may be operable to produce UV light, and the sensing means may sense any UV light produced by the at least one solid-state light source and reflected by at least one surface to the at least one reference location.

The apparatus may further include a means for reflecting any light produced by the at least one solid-state light source to the at least one reference location.

In accordance with a further illustrative embodiment of the invention, there is provided an apparatus for producing light output and for monitoring light output from the apparatus. The apparatus may include: at least one solid-state light source; and at least one light sensor positioned to sense any light produced by the at least one solid-state light source and reflected, by at least one surface spaced apart from the at least one solid-state light source, to at least one reference location spaced apart from the at least one surface.

The at least one light sensor may be operable to produce at least one sensor signal representing any light produced by the at least one solid-state light source and reflected by the at least one surface to the at least one reference location.

The apparatus may further include circuitry operable to produce at least one error signal in response to the sensor signal.

The circuitry may be operable to produce the at least one error signal in response to the sensor signal representing sensing no light produced by the at least one solid-state light source and reflected by the at least one surface to the at least one reference location.

The circuitry may be operable to produce the at least one error signal in response to the sensor signal representing sensing no light produced by the at least one solid-state light source and reflected by the at least one surface to the at least one reference location when an electric potential is applied across the at least one solid-state light source to cause the at least one solid-state light source to produce light.

The circuitry may be operable to produce the at least one error signal in response to the sensor signal representing sensing the level of light below a threshold level.

The circuitry may be operable to produce the at least one error signal in response to the sensor signal representing sensing the level of light below a threshold level when an electric potential is applied across the at least one solid-state light source to cause the at least one solid-state light source to produce light.

The at least one solid-state light source may be operable to produce UV light, and wherein the at least one light sensor is senses any UV light produced by the at least one solid-state light source and reflected by at least one surface to the at least one reference location.

The at least one light sensor may be a single light sensor.

The at least one solid-state light source may be a single solid-state light source.

The at least one reference location may be a single reference location.

The apparatus may further include at least one translucent body positioned to transmit a portion of any light produced by the at least one solid-state light source.

The at least one reference location may be outside of an entire space between the at least one solid-state light source and the at least one translucent body.

The at least one surface may include at least one surface of the at least one translucent body, and the at least one reference location may be positioned to receive at least some of any light produced by the at least one solid-state light source and reflected by the at least one surface of the at least one translucent body to the at least one reference location.

The at least one translucent body may include at least one lens.

The at least one translucent body may include at least one window.

The apparatus may further include at least one reflective body, the at least one surface may include at least one reflective surface of the at least one reflective body, and the at least one reference location may be positioned to receive at least some of any light produced by the at least one solid-state light source and reflected by the at least one reflective surface of the at least one reflective body to the at least one reference location.

The at least one reflective surface of the at least one reflective body may reflect any light produced by the at least one solid-state light source to the at least one reference location by specular reflection.

The at least one reflective surface of the at least one reflective body may reflect any light produced by the at least one solid-state light source to the at least one reference location by diffuse reflection.

The apparatus may further include at least one opaque body, the at least one surface may include at least one reflective surface of the at least one opaque body, and the at least one reference location may be positioned to receive at least some of any light produced by the at least one solid-state light source and reflected by the at least one reflective surface of the at least one opaque body to the at least one reference location.

The at least one reflective surface of the at least one opaque body may reflect any light produced by the at least one solid-state light source to the at least one reference location by specular reflection.

The at least one reflective surface of the at least one opaque body may reflect any light produced by the at least one solid-state light source to the at least one reference location by diffuse reflection.

The apparatus may further include an optical head comprising the at least one solid-state light source and the at least one reference location, the at least one surface may include at least one surface of the optical head.

The at least one solid-state light source and the at least one reference location may be on a same device.

The apparatus may further include a PCB, and the at least one solid-state light source and the at least one reference location may be on the PCB.

The at least one solid-state light source may include at least one LED.

The apparatus may further include a reaction chamber positioned to receive light from the at least one solid-state light source.

The reaction chamber may include a fluid conduit.

The at least one surface may include at least one surface of the reaction chamber.

In accordance with a further illustrative embodiment of the invention, there is provided a method of treating a fluid in the reaction chamber. The method may include subjecting the fluid to light from the at least one solid-state light source.

In various embodiments the fluid may include air. In other embodiments the fluid may include water.

Other aspects and features will become apparent to those ordinarily skilled in the art upon review of the following description of illustrative embodiments in conjunction with the accompanying figures.

DETAILED DESCRIPTION

Figure 1:
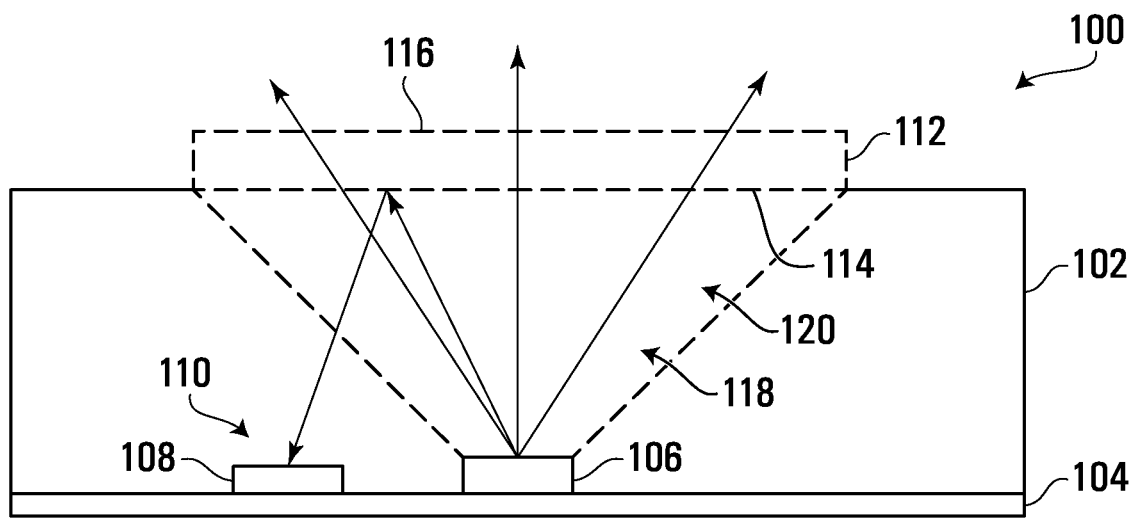
FIG. 1 is a cross-sectional view of an apparatus according to one embodiment.

Referring to FIG. 1, an apparatus according to one embodiment is shown generally at 100 and includes an optical head 102. The optical head 102 includes a printed circuit board ("PCB") 104, which includes a light-emitting diode ("LED") 106 and a light sensor 108. The LED 106 and the light sensor 108 are therefore on a same PCB and on a same device, which may allow the optical head 102 to occupy a relatively small footprint. The light sensor 108 senses light received at a reference location shown generally at 110 and proximate the light sensor 108. The optical head 102 also includes a window 112 having an inner surface 114 and an outer surface 116 opposite the inner surface 114. Windows such as those described herein may be made of quartz, fused silica, sapphire, calcium fluoride, and/or magnesium fluoride, for example.

In the embodiment shown, the LED 106 and the light sensor 108 face the inner surface 114 of the window 112, and the window 112 is within an output field or view angle shown generally at 118 of the LED 106. As a result, the window 112 is positioned to receive at least a portion of light produced by the LED 106 at the inner surface 114. However, alternative embodiments may differ. For example, alternative embodiments may omit the PCB 104 or may include alternatives to PCB 104, and in alternative embodiments the LED 106 and the light sensor 108 a different but same device. Further, alternative embodiments may include alternatives to the LED 106, which may include other solid-state light sources, for example. Further, alternative embodiments may include alternatives to the window 112, which may include one or more different windows, one or more lenses and/or one or more other optical components, or one or more other translucent bodies. Herein, a "translucent body" includes a "transparent body" and in various embodiments includes any body that transmits and/or diffuses some or all light received by the body. Further, alternative embodiments may include more than one LED, more than one light sensor, and/or one or more LEDs and one or more light sensors that may be positioned differently from the positions shown in FIG. 1. For example, one or more light sensors may be positioned to receive a desired amount or type of reflection from at least one solid-state light source.

In the embodiment shown, the LED 106 produces ultraviolet ("UV") light, the light sensor 108 senses UV light, and the window 112 is transparent to UV light. Therefore, "light" herein is not limited to visible light, but rather may include other electromagnetic radiation that may not necessarily be visible. Further, in the embodiment shown, the window 112 is positioned to transmit at least a portion of light produced by the LED 106 and received at the inner surface 114. However, alternative embodiments may differ. For example, in alternative embodiments, the LED 106 may produce light that is not necessarily UV light, the light sensor 108 may sense any such light produced by the LED 106, and the window 112 may be transparent to any such light produced by the LED 106.

Figure 2:
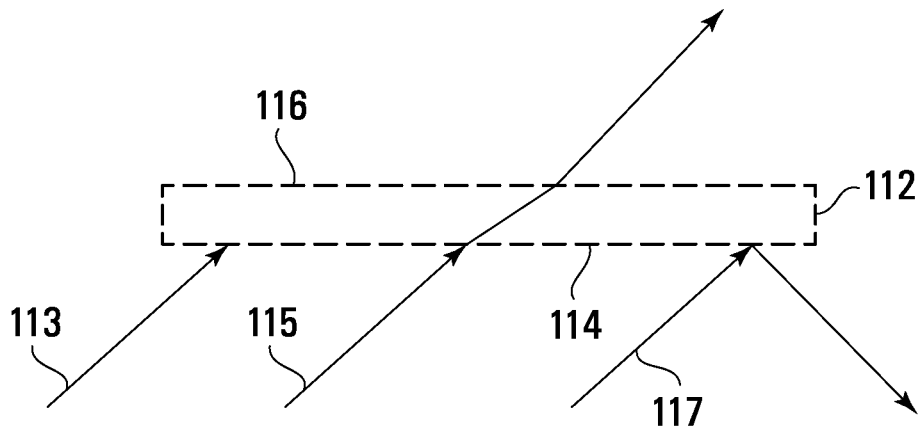
FIG. 2 is a side view of a window of the apparatus of FIG. 1.

Referring to FIG. 2, when light is received at the inner surface 114 of the window 112, a portion (shown at 113) of such light may be absorbed by the window 112, a portion (shown at 115) of such light may be transmitted (or refracted and transmitted) by the window 112, and a portion (shown at 117) of such light may be reflected by the window 112. Referring back to FIG. 1, at least a portion of light reflected by the window 112 may be received at the reference location 110 and sensed by the light sensor 108.

The LED 106 and the window 112 define a space or region shown generally at 120 between the LED 106 and the window 112 and through which space or region 120 light transmitted by the LED 106 travels to the window 112. The light sensor 108 may be positioned entirely outside of the space or region 120. As a result, the light sensor 108 may be positioned to avoid blocking any light that may be transmitted from the LED 106 to the window 112.

Figure 3:
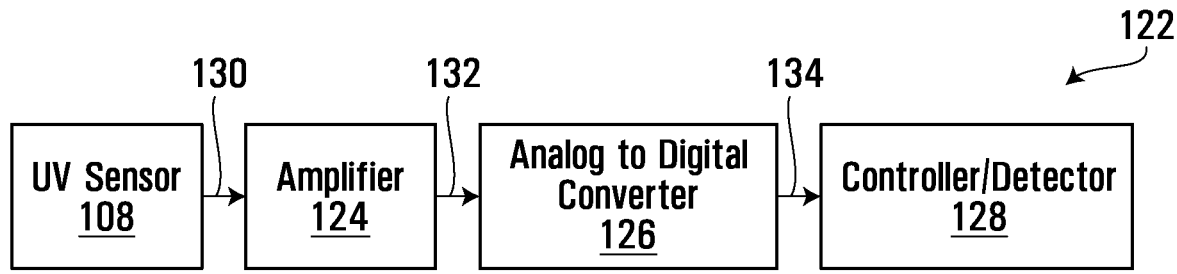
FIG. 3 is a schematic illustration of circuitry of the apparatus of FIG. 1.

Referring to FIG. 3, the apparatus 100 further includes circuitry shown generally at 122 including an amplifier 124, an analog-to-digital converter ("ADC") 126, and a controller 128. In the embodiment shown, the light sensor 108 produces an analog sensor signal 130 representing a level (such as an intensity or power level, for example) of light produced by the LED 106 and reflected by the inner surface 114 to the reference location 110. Also, in the embodiment shown, the amplifier 124 amplifies the analog sensor signal 130 to produce an amplified analog sensor signal 132, the ADC 126 converts the amplified analog sensor signal 132 to a digital sensor signal 134, and the controller 128 receives the digital sensor signal 134. The controller 128 may include a processor circuit including a microprocessor that may be programmed to function as described herein, for example.

The circuitry 122 shown is an example only, and alternative embodiments may include different circuitry. For example, the light sensor 108 may produce one or more analog and/or digital sensor signals that may represent, for example, sensing light produced by the LED 106 and reflected by the inner surface 114 to the reference location 110, sensing no light produced by the LED 106 and reflected by the inner surface 114 to the reference location 110, and/or a level (such as an intensity or power level, for example) of light produced by the LED 106 and reflected by the inner surface 114 to the reference location 110. Further, the amplifier 124 and/or the ADC 126 may be omitted or varied, and the controller 128 may include one or more processor circuits, one or more discrete logic circuits, and/or one or more application-specific integrated circuits ("ASICs"), for example.

The circuitry 122 may produce an error signal if one or more conditions are satisfied. For example, in some embodiments, the circuitry 122 may produce an error signal if the light sensor 108 senses no light produced by the LED 106 and reflected by the inner surface 114 to the reference location 110. Also, in some embodiments, the circuitry 122 may produce an error signal if the light sensor 108 senses no light produced by the LED 106 and reflected by the inner surface 114 to the reference location 110 when an electric potential is applied across the LED 106 to cause the LED 106 to produce light. Also, in some embodiments, the circuitry 122 may produce an error signal if the light sensor 108 senses a level of light produced by the LED 106 and reflected by the inner surface 114 to the reference location 110 that is below a threshold level. Also, in some embodiments, the circuitry 122 may produce an error signal if the light sensor 108 senses a level of light produced by the LED 106 and reflected by the inner surface 114 to the reference location 110 that is below a threshold level when an electric potential is applied across the LED 106 to cause the LED 106 to produce light.

Figure 4:
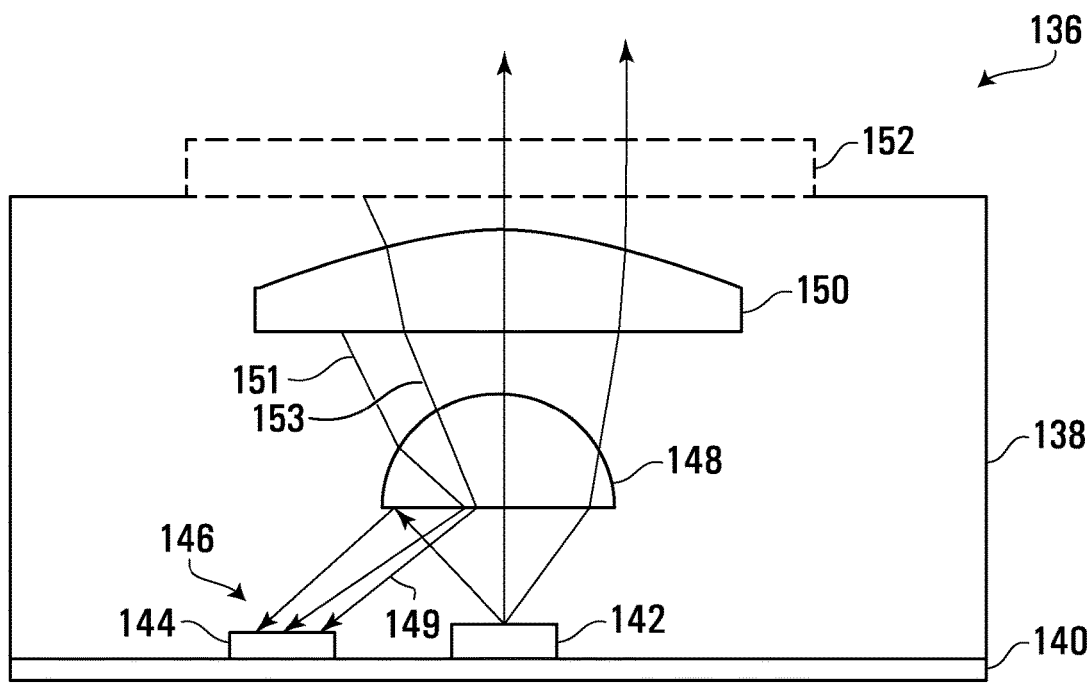
FIG. 4 is a cross-sectional view of an apparatus according to another embodiment.

The apparatus 100 shown is an example only, and alternative embodiments may vary. For example, referring to FIG. 4, an apparatus according to another embodiment is shown generally at 136 and includes an optical head 138. The optical head 138 includes a PCB 140, which includes an LED 142 and a light sensor 144. The light sensor 144 senses light received at a reference location shown generally at 146 and proximate the light sensor 144. The optical head 138 also includes a first lens 148, a second lens 150, and a window 152. In various embodiments, lenses may include one or more of plano-convex, ball and half-ball, cylindrical and/or concave lenses, or other types of lenses, for example. Further, lenses or other optical components such as those described herein may be made of quartz, fused silica, sapphire, calcium fluoride, and/or magnesium fluoride, for example.

As with the apparatus 100, the LED 142 may produce ultraviolet ("UV") light, the light sensor 144 may sense UV light, and the first lens 148, the second lens 150, and the window 152 may be transparent to UV light, but alternative embodiments may differ and may for example function as described above with light that is not necessarily UV light. Light from the LED 142 may be reflected by one or more surfaces of the first lens 148, by one or more surfaces of the second lens 150, and/or by one or more surfaces of the window 152 to the reference location 146. For example, light shown at 149 from the LED 142 may be reflected by a surface of the first lens 148 to the reference location 146. As another example, light shown at 151 and 153 may be reflected by a surface of the second lens 150 and then refracted and/or transmitted by the first lens 148 to the reference location 146. Otherwise the apparatus 136 may function similarly to the apparatus 100 as described above, for example.

Figure 5:
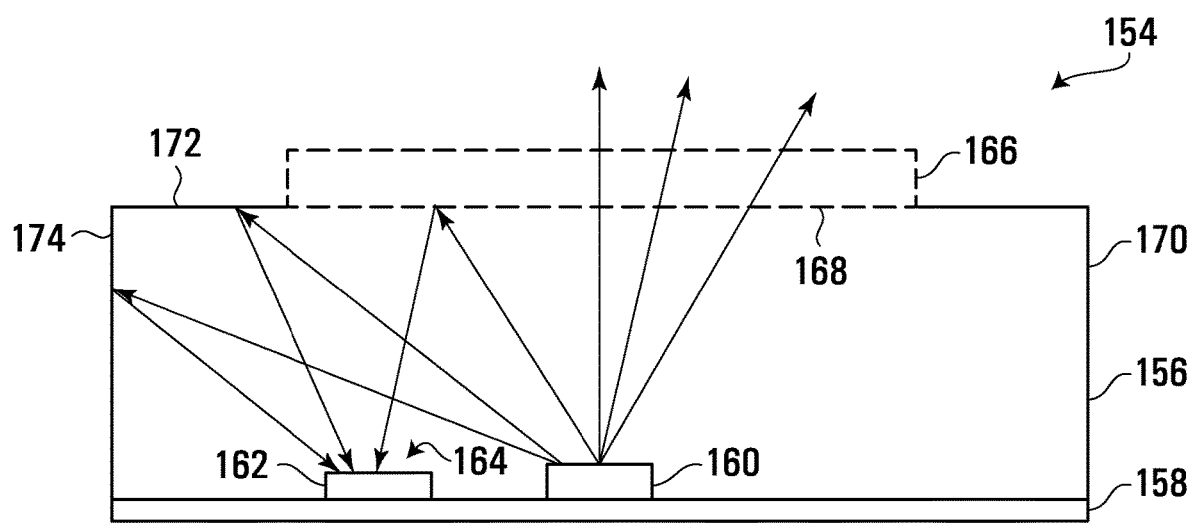
FIG. 5 is a cross-sectional view of an apparatus according to another embodiment.

As another example, referring to FIG. 5, an apparatus according to another embodiment is shown generally at 154 includes an optical head 156. The optical head 156 includes a PCB 158, which includes an LED 160 and a light sensor 162. The light sensor 162 senses light received at a reference location shown generally at 164 and proximate the light sensor 162. The optical head 156 also includes a window 166 having an inner surface 168. The optical head 156 also includes a housing 170 that may include reflective and/or opaque bodies and that has inner surfaces, such as an inner surface 172 adjacent the window 166 and an inner surface 174 perpendicular to the inner surface 172. The inner surfaces 172 and 174 may be reflective surfaces that may reflect light from the LED 160, and the inner surfaces 172 and 174 may reflect light from the LED 160 by specular reflection and/or by diffuse reflection. In general, such additional reflective surfaces may increase light reflected to the light sensor 162 and increase sensitivity of the light sensor 162.

As with the apparatus 100, the LED 160 may produce UV light, the light sensor 162 may sense UV light, and the first lens 148, the second lens 150, the window 166 may be transparent to UV light, and the inner surfaces 172 and 174 may reflect UV light, but alternative embodiments may differ and may for example function as described above with light that is not necessarily UV light. Light from the LED 160 may be reflected by the inner surface 168, by the inner surface 172, and/or by the inner surface 174 to the reference location 164, and otherwise the apparatus 154 may function similarly to the apparatus 100 as described above, for example.

Figure 6:
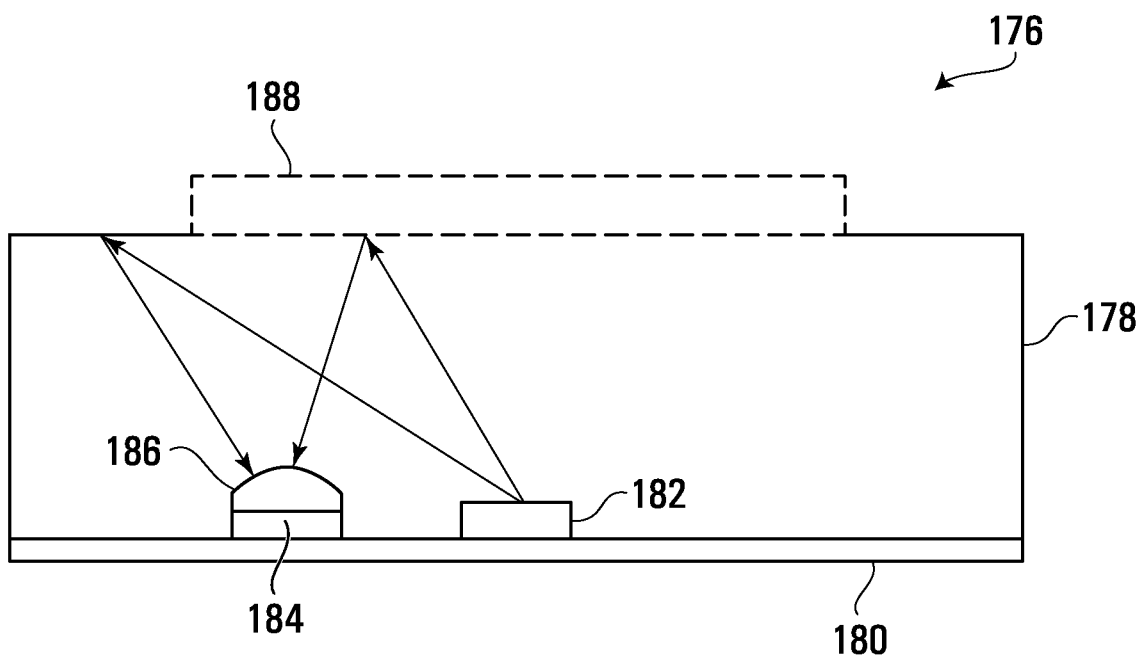
FIG. 6 is a cross-sectional view of an apparatus according to another embodiment.

As another example, referring to FIG. 6, an apparatus according to another embodiment is shown generally at 176 and includes an optical head 178. The optical head 178 includes a PCB 180, which includes an LED 182 and a UV sensor 184. The apparatus 176 is similar to the apparatus 100 except that the apparatus 176 includes an optical lens 186 (which may be a half-ball, a dome lens, or a converging lens, for example) on the UV sensor 184. In general, such an optical lens 186 may collect reflected light and may increase reflected light directed to the UV sensor 184 and increase sensitivity of the UV sensor 184. FIG. 6 illustrates a quartz window 188, although alternative embodiments may include one or more different translucent bodies. Further, although FIG. 6 illustrates a UV sensor 184, alternative embodiments may include different light sensors.

Figure 7:
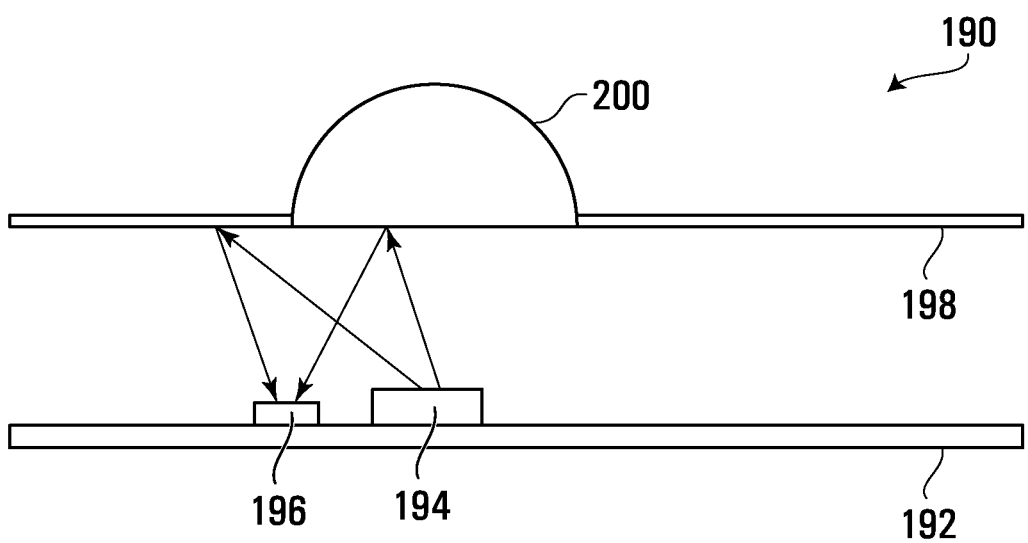
FIG. 7 is a cross-sectional view of an apparatus according to another embodiment.

As another example, referring to FIG. 7, an apparatus according to another embodiment is shown generally at 190 and includes a PCB 192 including an LED 194 and a UV sensor 196. The apparatus 190 also includes a reflective surface 198 and an optical lens 200, and is similar to the apparatus 100. Although FIG. 7 illustrates one optical lens 200, alternative embodiments may include one or more different translucent bodies. Further, although FIG. 7 illustrates a UV sensor 196, alternative embodiments may include different light sensors.

Figure 8:
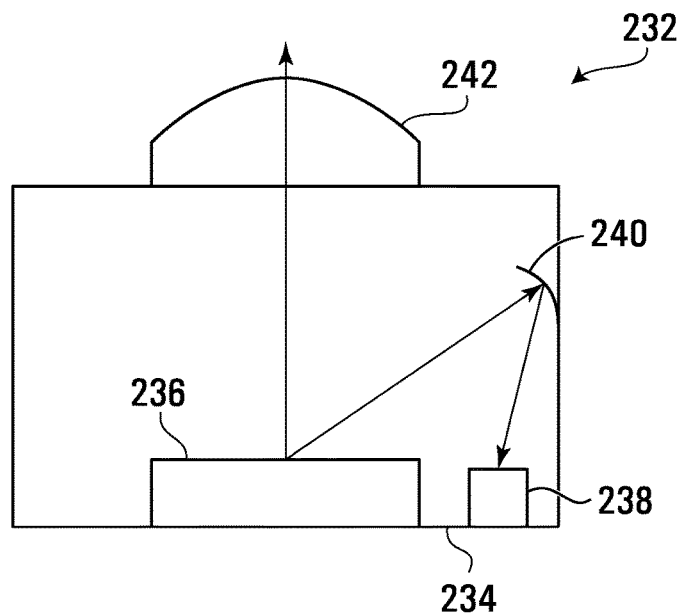
FIG. 8 is a cross-sectional view of an apparatus according to another embodiment.

As another example, referring to FIG. 8, an apparatus according to another embodiment is shown generally at 232 and includes a PCB 234 including an LED 236 and a UV sensor 238. The apparatus 232 also includes a reflective surface 240 and an optical lens 242, and is similar to the apparatus 100. Although FIG. 8 illustrates one optical lens 242, alternative embodiments may include one or more different translucent bodies. Further, although FIG. 8 illustrates a UV sensor 238, alternative embodiments may include different light sensors.

Figure 9:
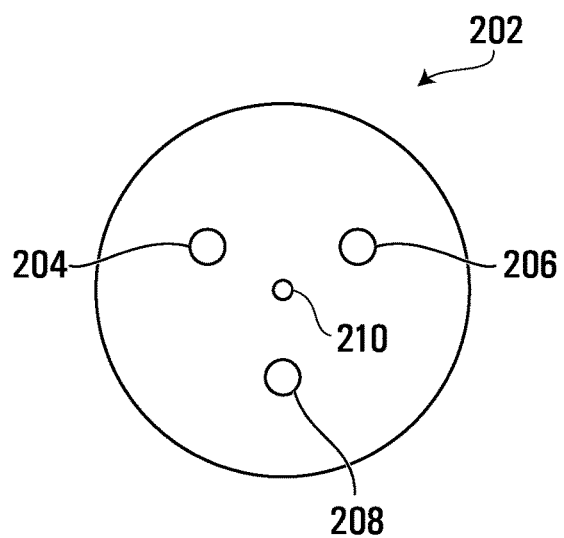
FIG. 9 is a plan view of an apparatus according to another embodiment.

The embodiments described above each include one LED, but alternative embodiments may include more than one LED. For example, referring to FIG. 9, an apparatus according to another embodiment is shown generally at 202 and includes three LEDs 204, 206, and 208 and one light sensor 210. The light sensor 210 may sense, at a reference location proximate the light sensor 210, any light produced by one or more of the LEDs 204, 206, and 208 and reflected by at least one surface spaced apart from the at least one solid-state light source and from the reference location. As a result, the apparatus 202 may monitor light output from the LEDs 204, 206, and 208 collectively, and more generally, the apparatus 202 may monitor collective light output from more than one light source. Of course, alternative embodiments may differ. For example, alternative embodiments may include fewer or more than three LEDs that may be positioned differently from the positions shown in FIG. 9.

Figure 10:
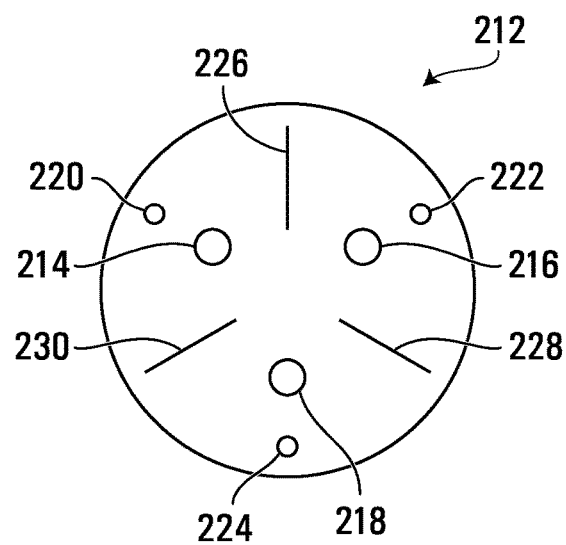
FIG. 10 is a plan view of an apparatus according to another embodiment.

As another example, referring to FIG. 10, an apparatus according to another embodiment is shown generally at 212 and includes three LEDs 214, 216, and 218. A light sensor 220 is positioned to sense, at a reference location proximate the light sensor 220, any light produced by the LED 214 and reflected by at least one surface spaced apart from the at least one solid-state light source and from the reference location proximate the light sensor 220. Further, a light sensor 222 is positioned to sense, at a reference location proximate the light sensor 222, any light produced by the LED 216 and reflected by at least one surface spaced apart from the at least one solid-state light source and from the reference location proximate the light sensor 222. Further, a light sensor 224 is positioned to sense, at a reference location proximate the light sensor 224, any light produced by the LED 218 and reflected by at least one surface spaced apart from the at least one solid-state light source and from the reference location proximate the light sensor 224. Further, an opaque body 226 optically isolates the LED 214 and the light sensor 220 from the LED 216 and 222, an opaque body 228 optically isolates the LED 216 and the light sensor 222 from the LED 218 and the light sensor 224, and an opaque body 230 optically isolates the LED 218 and the light sensor 224 from the LED 214 and the light sensor 220. As a result, the apparatus 212 may monitor light output from the LEDs 214, 216, and 218 independently. More generally, the apparatus 212 includes light sources associated with respective different light sensors and may therefore monitor light output from more than one light source independently.

However, alternative embodiments may differ. For example, some embodiments may omit some or all of the opaque bodies 226, 228, and 230, or one or more opaque bodies may differ in alternative embodiments. As another example, alternative embodiments may include fewer or more than three LEDs and fewer or more than three light sensors, and LEDs and light sensors according to alternative embodiments may be positioned differently from the positions shown in FIG. 10.

Figure 11:
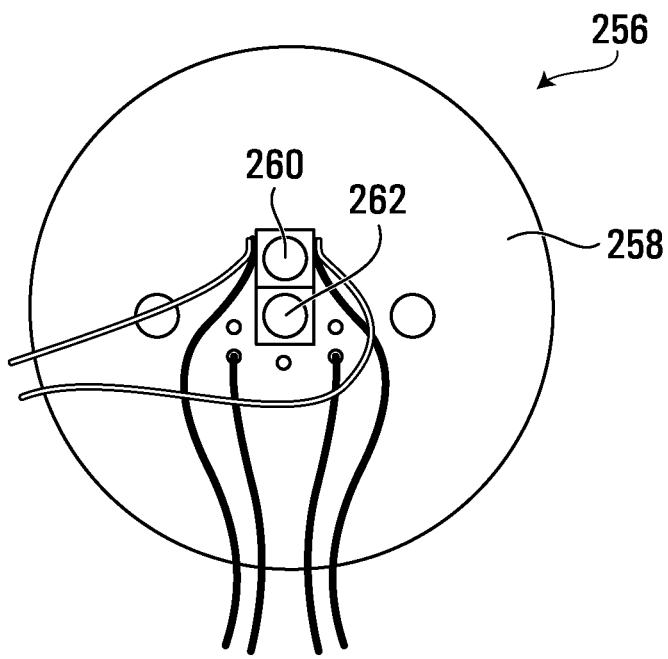
FIG. 11 is a plan view of an apparatus according to another embodiment.

As another example, referring to FIG. 11, an apparatus according to another embodiment is shown generally at 256, is similar to the apparatus 100, 136, or 154, for example, and includes a PCB 258, a light sensor (or UV sensor) 260, and an LED (or UV-LED) 262.

The embodiments described above are examples only, and embodiments described above may be varied or combined with other embodiments in many ways. For example, alternative embodiments may include alternatives to LEDs, which may include other solid-state light sources, for example. Also, the reflective surfaces of the embodiments described above are examples only, and alternative embodiments may omit such reflective surfaces, or alternative embodiments may include reflective surfaces that may be positioned, angled, and/or shaped differently from those of the embodiments described above. Further, the translucent bodies described above are examples only, and alternative embodiments may include omit such translucent bodies or may include one or more translucent bodies that may be similar to or different from the translucent bodies of the embodiments described above. For example, reflective surfaces and/or translucent bodies such as windows, lenses, or other optical components may be positioned, angled, coated (for example with one or more UV-reflective, UV-anti-reflective, light-reflective, and/or light-anti-reflective coatings, for example), treated, and/or shaped to obtain a desired amount or type of reflection from at least one solid-state light source to at least one reference location, to obtain a desired refraction-to-reflection radiation ratio, and/or more generally to obtain desired sensor performance.

Figure 12:
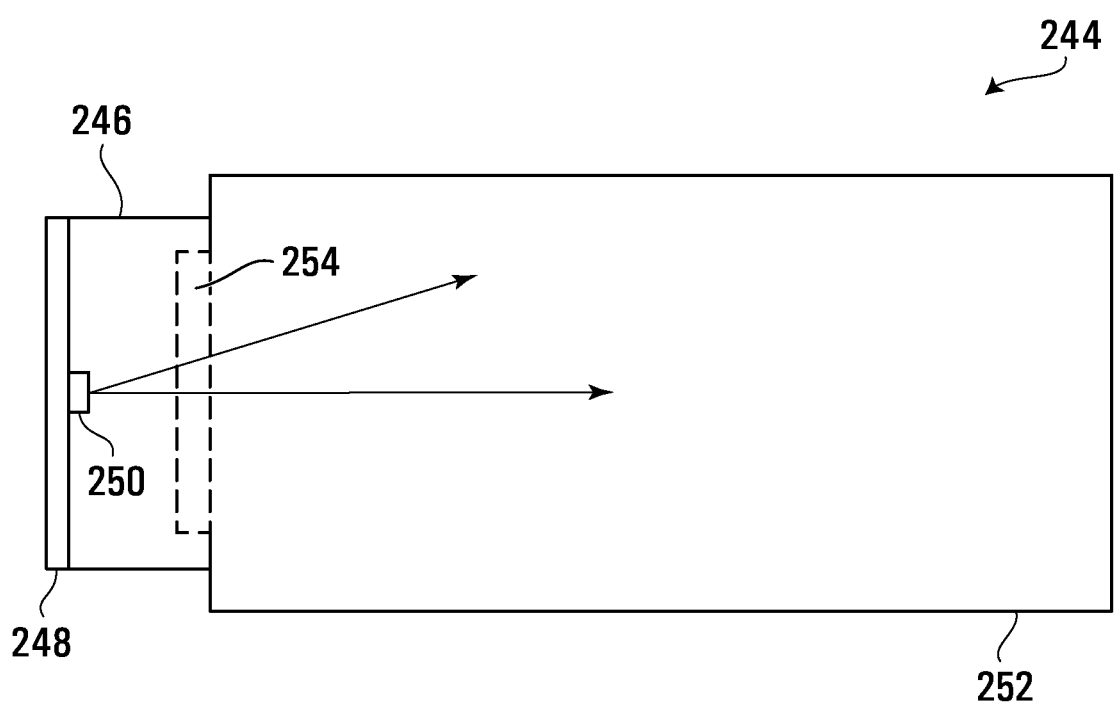
FIG. 12 is a cross-sectional view of an apparatus according to another embodiment.

Referring to FIG. 12, an apparatus according to another embodiment is shown generally at 244 and includes an optical head 246 (which may be similar to one of the optical heads described above, for example) including a PCB 248 including an LED 250. The apparatus 244 also includes a reaction chamber 252 positioned to receive light from the LED 250 of the optical head 246 through a UV-transparent window 254. Therefore, in some embodiments, one or more translucent bodies (such as the UV-transparent window 254, for example) may be an interface between an optical head (such as the optical head 246 or one of the other optical heads described above, for example) and a reaction chamber (such as the reaction chamber 252, for example) of a photo-reactor. In some embodiments, the reaction chamber may include a fluid conduit.

Figure 13:
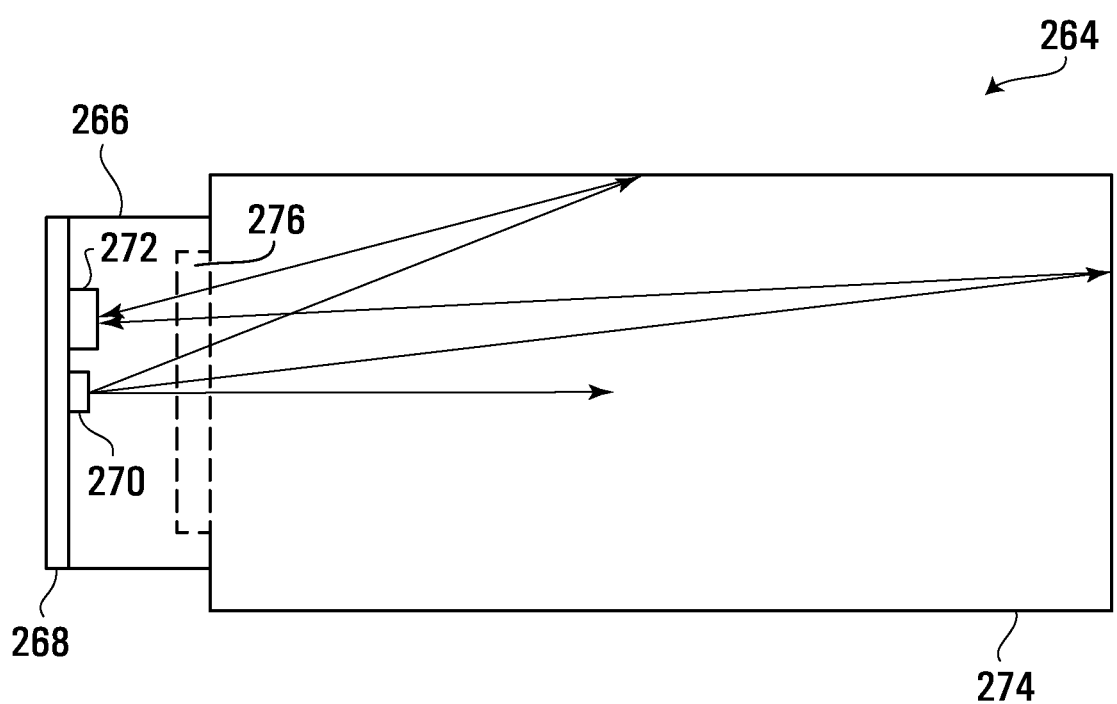
FIG. 13 is a cross-sectional view of an apparatus according to another embodiment.

Referring to FIG. 13, an apparatus according to another embodiment is shown generally at 264 and includes an optical head 266 (which may be similar to one of the optical heads described above, for example) including a PCB 268 including an LED 270 and a light sensor 272. The apparatus 264 also includes a reaction chamber 274 positioned to receive light from the LED 270 of the optical head 266 through a UV-transparent window 276. One or more internal surfaces of the reaction chamber 274 may be reflective to light (such as UV light, for example), and as shown in FIG. 13, at least a portion of light reflected by one or more internal surfaces of the reaction chamber 274 may be sensed by the light sensor 272.

Figure 14:
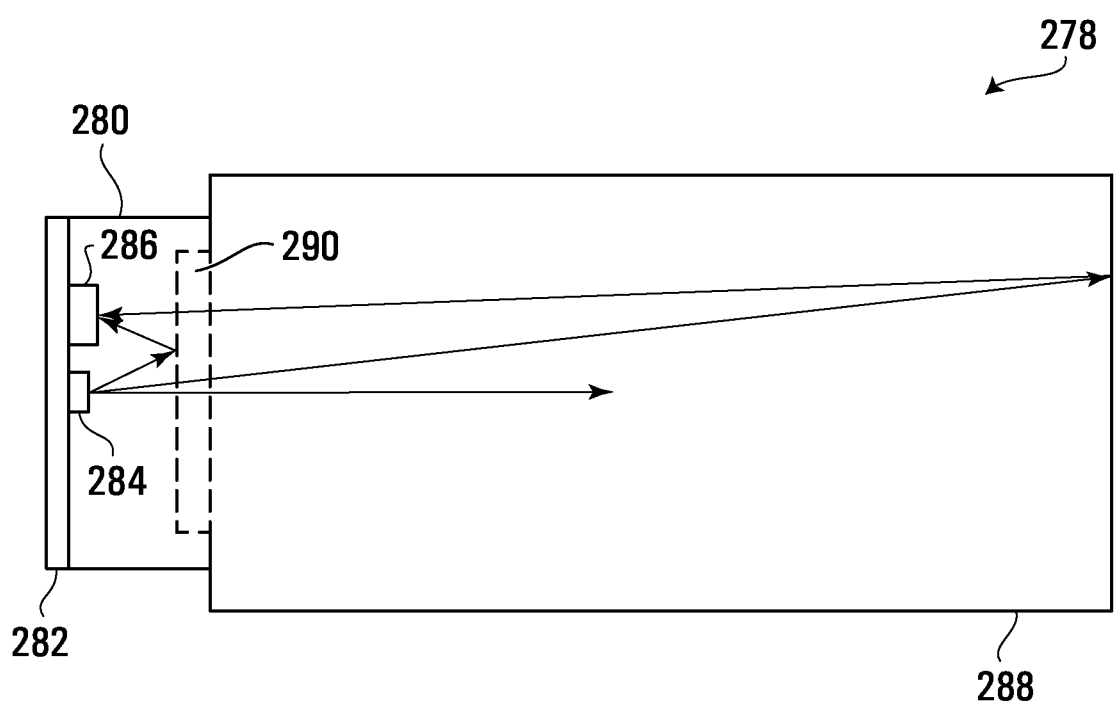
FIG. 14 is a cross-sectional view of an apparatus according to another embodiment.

Referring to FIG. 14, an apparatus according to another embodiment is shown generally at 278 and includes an optical head 280 (which may be similar to one of the optical heads described above, for example) including a PCB 282 including an LED 284 and a light sensor 286. The apparatus 278 also includes a reaction chamber 288 positioned to receive light from the LED 284 of the optical head 280 through a UV-transparent window 290. One or more internal surfaces of the reaction chamber 288 may be reflective to light (such as UV light, for example), and as shown in FIG. 14, at least a portion of light reflected by one or more internal surfaces of the reaction chamber 288 may be sensed by the light sensor 286. Further, at least a portion of light reflected by the UV-transparent window 290 may be sensed by the light sensor 286.

As shown in embodiments as described above, for example, light sensors such as those described herein may sense reflected light from one or more transparent bodies (such as one or more lenses and/or one or more windows) and/or from one or more reflective surfaces (which may include one or more surfaces of a reactor head, one or more surfaces of a reaction chamber, and/or one or more other surfaces).

In general, apparatuses such as those described above may include one or more reaction chambers and/or one or more fluid conduits, and optical heads such as those described above may be positioned such that one or more reaction chambers and/or one or more fluid conduits may be positioned to receive light from LEDs such as those described above. Therefore, fluid (such as air and/or water, for example) in one or more reaction chambers and/or one or more fluid conduits may receive or be subjected to light from LEDs such as those described above, and such fluid may be treated by subjecting such fluid to such light, which may include UV light for example.

In general, embodiments such as those described herein may include or cooperate with one or more photo-reactors, such as fluid treatment apparatuses for example, and monitor light output from at least one solid-state light source such as at least one LED, and embodiments such as those described herein may include apparatuses for producing light output and for monitoring light output from such apparatuses. For example, embodiments such as those described herein may monitor reflected light, which may otherwise have been wasted. Further, embodiments such as those described herein may produce one or more error signals, which may indicate that one or more LEDs have failed is/are failing, and which may prevent unknowingly failing to treat air and/or water in one or more fluid treatment apparatuses. Further, light sensors such as those described herein may be positioned entirely outside of an entire space (such as the space 120, for example) between at least one solid-state light source and at least one translucent body positioned to transmit a portion of any light produced by the at least one solid-state light source, which may avoid blocking any light that may be transmitted from the at least one solid-state light source to the at least one translucent body, and which may increase performance of a photo-reactor when compared to a photo-reactor in which a light sensor may block light that may be transmitted from at least one solid-state light source to at least one translucent body.

Although specific embodiments have been described and illustrated, such embodiments should be considered illustrative only and not as limiting the invention as construed according to the accompanying claims.

The invention claimed is:

1. A fluid treatment apparatus comprising:
at least one solid-state electromagnetic radiation source;
a reaction chamber positioned to receive electromagnetic radiation from the at least one solid-state electromagnetic radiation source to subject a fluid in the reaction chamber to the electromagnetic radiation; and
at least one electromagnetic radiation sensor positioned to sense any electromagnetic radiation produced by the at least one solid-state electromagnetic radiation source and reflected, by at least one surface spaced apart from the at least one solid-state electromagnetic radiation source, to at least one reference location spaced apart from the at least one surface.

2. The apparatus of claim 1 wherein the at least one electromagnetic radiation sensor is operable to produce at least one sensor signal representing any electromagnetic radiation produced by the at least one solid-state electromagnetic radiation source and reflected by the at least one surface to the at least one reference location.

3. The apparatus of claim 2 further comprising circuitry operable to produce at least one error signal in response to the sensor signal representing sensing no electromagnetic radiation produced by the at least one solid-state electromagnetic radiation source and reflected by the at least one surface to the at least one reference location.

4. The apparatus of claim 2 further comprising circuitry operable to produce at least one error signal in response to the sensor signal representing sensing the level of electromagnetic radiation below a threshold level.

5. The apparatus of claim 1 wherein the at least one solid-state electromagnetic radiation source is operable to produce ultraviolet (UV) electromagnetic radiation, and wherein the at least one electromagnetic radiation sensor senses any UV electromagnetic radiation produced by the at least one solid-state electromagnetic radiation source and reflected by at least one surface to the at least one reference location.

6. The apparatus of claim 1 further comprising at least one translucent body positioned between the at least one solid-state electromagnetic radiation source and the reaction chamber to transmit a portion of any electromagnetic radiation produced by the at least one solid-state electromagnetic radiation source into the reaction chamber.

7. The apparatus of claim 6 wherein the at least one reference location is outside of an entire space between the at least one solid-state electromagnetic radiation source and the at least one translucent body.

8. The apparatus of claim 6 wherein the at least one surface comprises at least one surface of the at least one translucent body, and wherein the at least one reference location is positioned to receive at least some of any electromagnetic radiation produced by the at least one solid-state electromagnetic radiation source and reflected by the at least one surface of the at least one translucent body to the at least one reference location.

9. The apparatus of claim 1 further comprising at least one reflective body, wherein the at least one surface comprises at least one reflective surface of the at least one reflective body, and wherein the at least one reference location is positioned to receive at least some of any electromagnetic radiation produced by the at least one solid-state electromagnetic radiation source and reflected by the at least one reflective surface of the at least one reflective body to the at least one reference location.

10. The apparatus of claim 9 wherein the at least one reflective surface of the at least one reflective body reflects any electromagnetic radiation produced by the at least one solid-state electromagnetic radiation source to the at least one reference location by specular reflection.

11. The apparatus of claim 9 wherein the at least one reflective surface of the at least one reflective body reflects any electromagnetic radiation produced by the at least one solid-state electromagnetic radiation source to the at least one reference location by diffuse reflection.

12. The apparatus of claim 1 further comprising at least one opaque body, wherein the at least one surface comprises at least one reflective surface of the at least one opaque body, and wherein the at least one reference location is positioned to receive at least some of any electromagnetic radiation produced by the at least one solid-state electromagnetic radiation source and reflected by the at least one reflective surface of the at least one opaque body to the at least one reference location.

13. The apparatus of claim 1 further comprising an optical head comprising the at least one solid-state electromagnetic radiation source and the at least one reference location, wherein the at least one surface comprises at least one surface of the optical head.

14. The apparatus of claim 1 wherein the at least one solid-state electromagnetic radiation source and the at least one reference location are on a same device.

15. The apparatus of claim 1 further comprising a printed circuit board (PCB), wherein the at least one solid-state electromagnetic radiation source and the at least one reference location are on the PCB.

16. The apparatus of claim 1 wherein the reaction chamber comprises a fluid conduit.

17. The apparatus of claim 1 wherein the at least one surface comprises at least one surface of the reaction chamber.

18. A method of treating a fluid in the reaction chamber of the apparatus of claim 1, the method comprising:
subjecting the fluid to electromagnetic radiation from the at least one solid-state electromagnetic radiation source.

19. The method of claim 18 wherein the fluid comprises water.

20. The apparatus of claim 1 further comprising an optical head comprising the at least one solid-state electromagnetic radiation source and the at least one reference location, wherein the at least one solid-state electromagnetic radiation source and the at least one electromagnetic radiation sensor are in a same compartment of the optical head.

* * * * *